US010945443B2

(12) United States Patent
Vinuesa Navarro et al.

(10) Patent No.: US 10,945,443 B2
(45) Date of Patent: Mar. 16, 2021

(54) TOLYPOCLADIUM ALBUM STRAIN

(71) Applicants: Valent BioSciences LLC, Libertyville, IL (US); Instituto Biomar, S.A., Leon (ES)

(72) Inventors: Maria de los Angeles Vinuesa Navarro, Leon (ES); Jose Maria Sanchez Lopez, Leon (ES); Deanna Branscome, Lake Villa, IL (US); Emily E. Brazil, Gurnee, IL (US); Rebecca Dickenson, Volo, IL (US); Daniel F. Heiman, Libertyville, IL (US); Gary T. Wang, Libertyville, IL (US); Zuoxing Zheng, Buffalo Grove, IL (US); Daniel C Leep, Lindenhurst, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

(21) Appl. No.: 16/141,188

(22) Filed: Sep. 25, 2018

(65) Prior Publication Data

US 2019/0098904 A1 Apr. 4, 2019

Related U.S. Application Data

(60) Provisional application No. 62/566,033, filed on Sep. 29, 2017.

(51) Int. Cl.
*A01N 63/30* (2020.01)
*C12R 1/645* (2006.01)
*C12N 1/14* (2006.01)

(52) U.S. Cl.
CPC ............... *A01N 63/30* (2020.01); *C12N 1/14* (2013.01); *C12R 1/645* (2013.01)

(58) Field of Classification Search
CPC ........... A01N 63/30; C12R 1/645; C12N 1/14
See application file for complete search history.

(56) References Cited

U.S. PATENT DOCUMENTS 5,656,459 A 8/1997 Balaraman et al.
5,747,330 A 5/1998 Casareto et al.

FOREIGN PATENT DOCUMENTS

WO 1994/016091 A1 7/1994

OTHER PUBLICATIONS

Motoyama et al., Chemistry & Biology, 2012, vol. 19, p. 1611-1619, and 11 pages of supplemental Information.*
NCBI Taxonomy browser search results forTolypocladium album, retrieved from NCBI website on Mar. 26, 2020, 2 pages of PDF.*
Quandt et al., IMA Fungus, 2014, vol. 5, No. 1, p. 121-134.*
Huang et al., The Journal of Antibiotics, 1995, vol. 48, No. 1, p. 1-4.*
International Search Report and Written Opinion dated Jan. 3, 2019.
Fukuda et al. "Tolypoalbin, a new tetramic acid from Tolypocladium album TAMA 479," the Journal of Antibiotics, Jan. 28, 2015 (Jan. 28, 2015), vol. 68, pp. 399-402.
Gazis et al. "Novel endophytic lineages of Tolypocladium provide new insights into the ecology and evolution of Cordyceps-like fungi," Mycologia, Jul. 1, 2014 (Jul. 1, 2014), vol. 106, Iss. 6, pp. 1090-1105.
Huang et al. "Terpendoles, Novel ACATInhibitors Produced by Albophoma yamanashiensis," the Journal of Antibiotics, Jan. 1, 1995 (Jan. 1, 1995), vol. 48, No. 1, pp. 5-11.
Motoyama et al. "Terpendole E. a Kinesin Eg5 Inhibitor, is a Key Biosynthetic Intermediate of Indole-Diterpenes in the Producing Fungus *Chaunopycnis alba*," Chemistry & Biology, Dec. 21, 2012 (Dec. 21, 2012), vol. 19, Iss. 2, pp. 1611-1619.

* cited by examiner

*Primary Examiner* — Kade Ariani
(74) *Attorney, Agent, or Firm* — Wood, Phillips, Katz, Clark & Mortimer

(57) ABSTRACT

A novel fungal strain of *Tolypocladium album* (synonym *Chaunopycnis alba*) is disclosed that has enhanced toxicity against insects and mites. This novel *Tolypocladium album* strain is capable of producing terpendoles A, C, I, J, K, N, O and P through fermentation and does not produce nalanthalide.

15 Claims, 2 Drawing Sheets

Specification includes a Sequence Listing.

FIG. 1

```
tttagaggaa gtaaaagtcg taacaaggtc tccgttggtg aaccagcgga gggatcatta    60
ccgagttatc aactcccaaa cccctgtgaa catacctgaa cgttgcctcg gcgggaccgc   120
cccggcgccc aactcgcggc ccggacccag gcgcccgccg gaggacccaa actcttgctt   180
taaacagtgg catactctct gagtctcaca aacaaaaaat gaatcaaaac tttcaacaac   240
ggatctcttg gctctggcat cgatgaagaa cgcagcgaaa tgcgataagt aatgtgaatt   300
gcagaattca gtgaatcatc gaatctttga acgcacattg cgcccgccag cattctggcg   360
ggcatgcctg tccgagcgtc atttcaaccc tcagggcccc ccttcgcggg ggggacctgg   420
tgttgggggc cggccgccct gcgcgcgccg ccccgaaat gcagtggcga cctcgccgca   480
gcctcccctg cgtagtagca caacctcgca ccggagcgcg gagacggtca cgccgtaaaa   540
cgcccaactt tcaagagttg acctcggatc ag                                572
```

FIG. 2
A
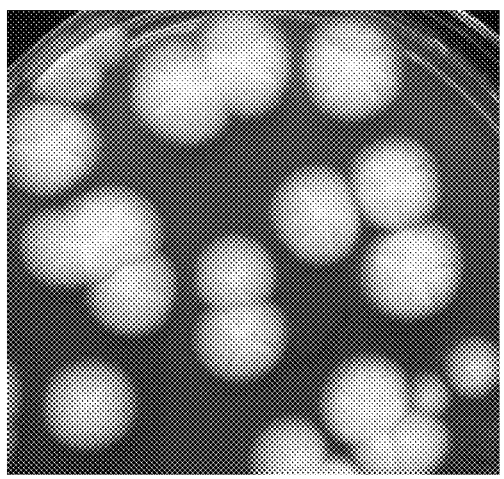
B
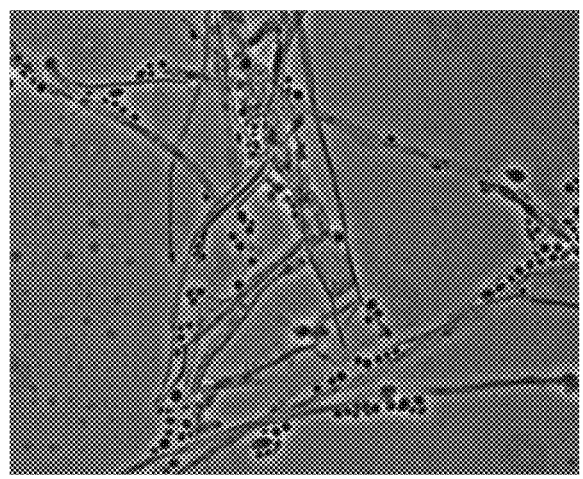

TOLYPOCLADIUM ALBUM STRAIN

FIELD OF THE INVENTION

The present invention relates to organisms producing biological pesticides. Specifically, the present invention relates to a novel strain of *Tolypocladium album* (synonym *Chaunopycnis alba*) that is capable of producing metabolites including terpendoles that are effective against a variety of insects and methods of their preparation and uses thereof.

BACKGROUND OF THE INVENTION

Arthropod pests, including insects and mites, are one of the major threats to human welfare, exert continued stress on the food supply and transmit a broad array of medical and veterinary diseases. Insect pests can cause severe and costly damage to crops, ornamental plants and stored foods. Further, insect and mite pests transmit diseases in and among humans resulting in reduced life expectancy, reduced quality of life and increased medical costs.

Aphids are highly problematic and costly pests of cultivated plants. There are approximately 250 described species of aphids that are known to eat crops, trees and ornamental plants. Aphids feed on the nectar of plants causing decreased growth rates, low yields and death. Aphids are also vectors for many microscopic plant pathogens spreading disease from plant to plant. Efforts to control aphids include synthetic pesticide application and the introduction of natural predators. While aphids have numerous natural predators such as ladybirds and parasitic wasps, predators and parasitoids alone are not effective at preventing crop plant damage by aphids. Unfortunately, aphids have developed resistance to many common synthetic pesticides. One particularly problematic aphid is the green peach aphids (*Myzus persicae*.) The green peach aphid is found worldwide and is a significant pest of peach trees and transmits plant viruses, such as potato virus Y and potato leafroll virus to member of the Solanaceae family.

Another costly insect pest is the whitefly. Like aphids, whiteflies feed on the nectar of plants and introduce plant pathogens through their saliva. Attempts to control whiteflies include synthetic pesticides and natural predators. However, whiteflies are particularly difficult to control as they readily develop resistance to synthetic pesticides and multiply too rapidly to be controlled by predators alone. One particularly problematic whitefly is the silverleaf whitefly (*Bemisia tabaci*.) The silverleaf whitefly is well distributed as it is found in geographies as varied as Australia, Africa, the United States and several European countries. In the 1980's a particularly virulent strain of silverleaf whiteflies was found in poinsettia crops in Florida. Within 5 years this silverleaf whitefly strain had spread to numerous other crops and has caused over $1 billion in damages to the agricultural industries across the United States. The silverleaf whitefly is also responsible for spreading plant viruses such as the tomato yellow leaf curl virus that causes premature ripening. The silverleaf whitefly has developed resistance to many common synthetic insecticides.

Mites are another pest of economic importance. Twospotted spider mites are of particular importance as they have been reported to infest more than 200 different plant species. These species include woody plants, ornamentals, fruit crops, vegetable crops and greenhouse crops. Mites feed by using their piercing-sucking mouthparts to extract sap from leaves. After leaves are pierced, chlorotic spots occur, eventually leading necrosis and possible defoliation. Mites have many natural enemies such as predatory mites (including *Phytoseiulus persimilis*, *Mesoseiulus longipes*, *Neoseiulus californicus*, *Galendromus occidentalis* and *Amblyseius fallicusare*) and insects (including *Scolothrips sexmaculatus*, *Stethorus picipes*, *Feltiella acarivora* and others). Unfortunately, natural insect predators are often killed by the use of broad spectrum insecticides. As a result, the over use of insecticides often leads to mite outbreaks, particularly when the weather is hot and dry. Various insecticides such as carbaryl, some organophosphates, and some pyrethroids have been suggested to favor spider mite populations by increasing nitrogen levels in leaves. In addition, some insecticides such as carbaryl have been reported to increase reproductive rate of mites. Additionally, prolonged use of synthetic acaricides often causes mites to develop resistance.

Synthetic pesticides have played a significant role in ushering in modern agriculture and pest control. However, there is increasing pressure from the public and from regulatory agencies to reduce or eliminate the exclusive use of synthetic chemical in the control of agricultural arthropod pests. The widespread use of relatively few available insecticides results in the development of resistant insect populations. Insecticide resistance is a complex phenomenon manifested in a diverse array of physiological mechanisms. Major mechanisms that are responsible for the development of insecticide resistance are metabolic detoxification, target site mutation, reduced cuticular penetration and behavioral avoidance. Novel natural insecticides are needed to combat the ever-increasing number of resistant insect species and populations.

Alternatives to synthetic pesticides and natural predators to control harmful insects and mites include microbial pesticides and biological pesticides. Microbial pesticides are in development and some have been put to commercial use. However, the number of microbial pesticides under manufacture and in use is limited.

Thus, there is a need in the art for alternative means to control insects and mites including microbial pesticides. These microbial pesticides should be capable of producing pesticidal metabolites that controls a variety of insects and mites.

SUMMARY OF THE INVENTION

The present invention is directed to a novel fungal strain of *Tolypocladium album*, HL-105-64-AC11. HL-105-64-AC11 that is capable of producing pesticidal metabolites via fermentation that can control a broad range of insects and mites. The fungal strain may be further characterized by its production of terpendoles including terpendole A, C, J, I, K, N, O and P. The fungal strain may be further characterized by the absence of nalanthalide production.

The present invention is further directed to a pesticidal composition comprising HL-105-64-AC11 or a fermentate produced by HL-105-64-AC11 and a suitable carrier.

The present invention is further directed to methods of controlling pests comprising applying an effective amount of HL-105-64-AC11 or a fermentate produced from HL-105-64-AC11 to a pest or the pest's environment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Internal transcribed spacer ("ITS") sequence (SEQ ID NO: 1) of *Tolypocladium album* strain HL-105-64-AC11.

FIG. 2. A. Morphology of colonies of *T. album* HL-105-64-AC11; B. Morphology of, mycelia and spores of *T. album* HL-105-64-AC11.

FIG. 3. Correlation coefficient of terpendoles isolated from *T. album* HL-105-64-AC11

DETAILED DESCRIPTION OF THE INVENTION

The present invention is generally directed to a novel, biologically pure strain of *T. album*, HL-105-64-AC11. This strain was deposited with the American Type Culture Collection in Manassas, Va. on Nov. 17, 2017 having accession number PTA-124560. HL-105-64-AC11 exhibits improved pesticidal activity as compared to other *T. album* strains. Specifically, HL-105-64-AC11 produces terpendole C when fermented. Further, unlike other *T. album* strains, HL-105-64-AC11 does not produce the toxic compound, nalanthalide when fermented.

The phrase "biologically pure fungal strain" as used herein means a strain essentially free from biological contamination and having a genetic uniformity such that different substrains taken therefrom will display substantially identical genotypes and phenotypes.

DNA sequencing including random amplification of polymorphic DNA ("RAPD"), may serve to characterize the genetic architecture of a strain and thus serve as a further identifier of the fungal strain of the invention.

Genetic identification was performed by sequencing of an ITS region of ribosomal DNA and comparison of obtained results with the ones published in genetic databases for genetic identification of this species.

The new fungal strain was identified as *Tolypocladium album* with 100% match with a *Tolypocladium album* isolate in a gene bank. *Tolypocladium album* can also be referred to *Chaunopycnis alba* as they are synonyms.

The results of genetic analysis of the ITS sequence from the strain *Tolypocladium album* strain HL-105-64-AC11 defined in this invention, are shown in FIG. 1 as SEQ ID NO:1. The strain is characterized by the lack of nalanthalide production as described in Example 1.

HL-105-64-AC11 strain of *T. album* may be produced by methods disclosed in the present application.

In one embodiment, the present invention is directed to a pesticidal composition comprising a mixture of an effective amount of HL-105-64-AC11 or a fermentate produced by HL-105-64-AC11 and a suitable carrier.

Compositions of the present invention may contain from about 0.1% by weight to about 99% by weight, preferably from about 0.1% by weight to about 95% by weight of HL-105-64-AC11 or a fermentate of HL-105-64-AC11 and from about 1% to about 99.9% by weight of an acceptable solid or liquid inert carrier.

As used herein, the term "fermentate" refers to the resulting product of the breakdown of a carbon source by HL-105-64-AC11 strain of *Tolypocladium album*. The fermentate may contain alcohols, fatty alcohols, organic acids, salts and other metabolites such as terpendole A, C, I, J, K, N, O and P. The fermentate may be differentiated from other *T. album* strains by its lack of production of nalanthalide. See Example 1, below.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will kill the target pest. The "effective amount" will vary depending on the mixture concentration, the type of pest(s) being treated, the severity of the pest infestation, the result desired, and the life stage of the pest during treatment, among other factors. Thus, it is not always possible to specify an exact "effective amount." However, an appropriate "effective amount" in any individual case may be determined by one of ordinary skill in the art.

After production of the HL-105-64-AC11 strain of *T. album* according to the above methodology, large-scale fermentation may be carried out using media and fermentation techniques which are often optimized for improved yield as commonly practiced in the fermentation industry. The fermentation broth as a whole, or an extract from the HL-105-64-AC11 fermentate may then be concentrated, lyophilized, spray-dried and/or formulated in any of a number of well-known ways, including as a liquid concentrate, dry or wettable powder or suspension for spraying on or under foliage, and a granular preparation for application to soil or foliage. Alternatively, the fermentation broth may be formulated directly without extraction or other processing.

The phrase "acceptable carrier" as used herein means an otherwise inert filler or excipient which confers upon the composition desirable storability, material handling and application characteristics; commonly-used carriers may include fillers, binders, surfactants, dispersants, adhesion agents and the like.

The pesticidal compositions comprising HL-105-64-AC11 or a fermentate of HL-105-64-AC11 may be in the form of, for example, a suspension, a dispersion, an aqueous emulsion, a dusting powder, a dispersible powder, an emulsifiable concentrate, an aerosol or micro or microencapsulated granules or any other formulation that gives controlled release of *T. album*.

In another embodiment, the present invention is directed to a method of controlling a pest comprising applying an effective amount of HL-105-64-AC11 or a fermentate produced by HL-105-64-AC11 to a pest or the pest's environment.

As used herein, "controlling a pest" refers to decreasing the negative impact of the pest on plants or animals to a level that is desirable to the grower or animal.

As used herein, "pest's environment" refers to any area where the pest is present during any life stage. One environment likely to be treated by the methods of the present invention includes the plants that the pest is living on/in and the surrounding soil. The pest's environment may also include harvested plants, gardens, fields, greenhouses, or other buildings, and various indoor surfaces and structures, such as furniture including beds, and furnishings including books, clothing, etc.

The articles "a," "an" and "the" are intended to include the plural as well as the singular, unless the context clearly indicates otherwise. For example, the methods of the present invention are directed to controlling "pest" but this can include control of a multiple pests (such as a more than one insect or more than one insect species or more than one mite or more than one mite species).

As used herein "terpendole A" refers to the following structure

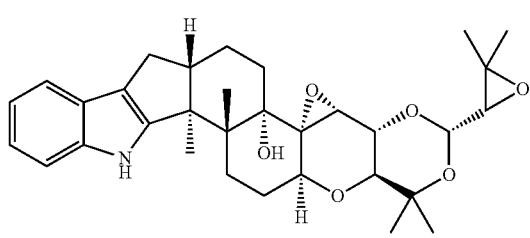

with CAS number 156967-65-5.

As used herein "terpendole C" refers to the following structure

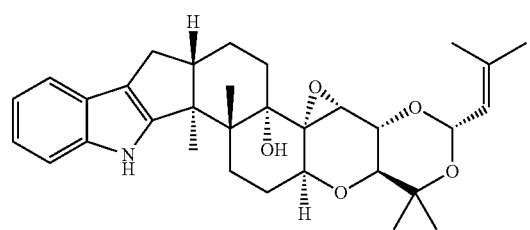

with CAS number 156967-64-6.

As used herein "terpendole I" refers to the following structure

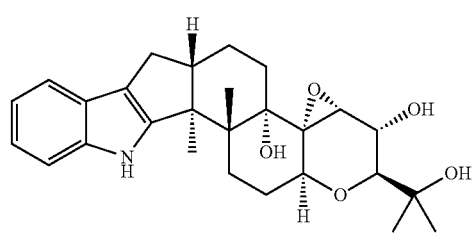

with CAS number 167612-17-1.

As used herein "terpendole J" refers to the following structure

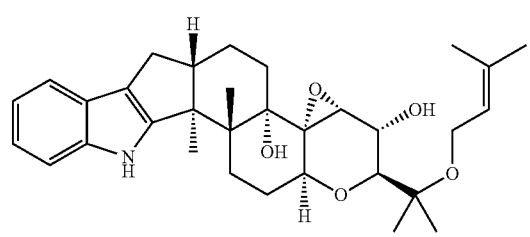

with CAS number 167427-26-1.

As used herein "terpendole K" refers to the following structure

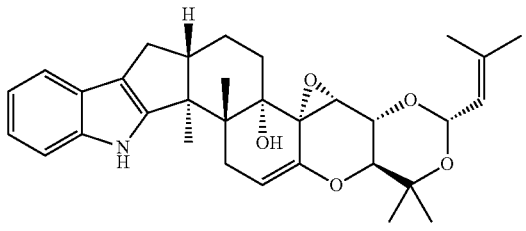

with CAS number 167427-27-2.

As used herein "terpendole N" refers to the following structure

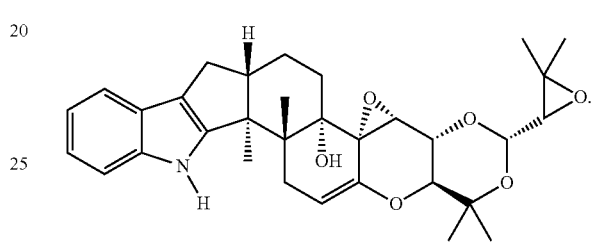

As used herein "terpendole O" refers to the following structure

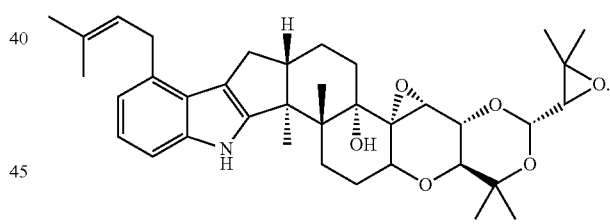

As used herein "terpendole P" refers to the following structure

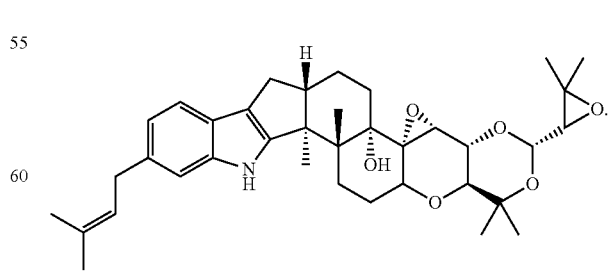

As used herein "nalanthalide" refers to the following structure

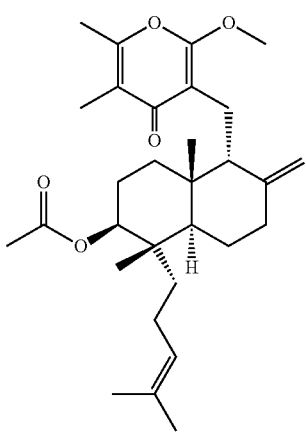
having CAS number 145603-76-5.

The pesticidal compositions of the invention can be applied directly to the plant by, for example, spraying or dusting an effective amount of the HL-105-64-AC11 or the HL-105-64-AC11 fermentate at the time or after the pest has begun to appear on the plant or before the appearance of pests as a protective measure. Plants to be protected within the scope of the present invention include, but are not limited to, cereals (wheat, barley, rye, oats, rice, sorghum and related crops), beet (sugar beet and fodder beet), drupes, pomes and soft fruit (apples, pears, plums, peaches, almonds, cherries, strawberries, raspberries, and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fiber plants (cotton, flax, hemp, jute), citrus fruit (oranges, lemons, grapefruit, mandarins), vegetables (spinach, lettuce, asparagus, cabbages and other brassicae, carrots, onions, paprika), lauraceae (avocados, cinnamon, camphor), solanaceae (potato, tomato, eggplant, chili peppers, bell peppers, ground cherries, tomatillos, cape gooseberry, wolfberry, Chinese lantern, petunia, browallia, hyacinth, mandrake, deadly nightshade, tobacco), deciduous trees and conifers (linden-trees, yew-trees, oak-trees, alders, poplars, birch-trees, firs, larches, pines), or plants such as maize, tobacco, nuts, coffee, sugar cane, tea, vines hops, bananas and natural rubber plants, as well as ornamentals. The preferred mode of application is by foliar spraying. It is generally important to obtain good control of pests in the early stages of plant growth as this is the time when the plant can be most severely damaged. The spray or dust can conveniently contain another insecticide or pesticide, e.g., fungicide, grass herbicide or fertilizer, if this is thought necessary. In a preferred embodiment, the composition of the invention is applied directly to the plant.

The compositions of the present invention are effective against arthropods. As used herein "arthropod" refers to pests that belong with Phylum Arthropoda. In a preferred embodiment, the pests are insects. As used herein, "insect" refers to pests that belong to the Class Insecta. In another preferred embodiment, the pests are mites. As used herein, "mite" refers to pests that belong to the Subclass Acari of the Class Arachnida.

In another preferred embodiment, the pest is an aphid. As used herein, "aphid" refers to pests that belong to the Family Aphididae. Exemplary aphids include cotton aphid (*Aphis gossypii*), foxglove aphid (*Aulacorthum solani*), cabbage aphid (*Brevicoryne brassicae*), birdcherry-oat aphid (*Rhopalosiphum padi*) and green peach aphid (*Myzus persicae*).

In another preferred embodiment, the pest is a lepidopteran. As used herein, "lepidopteran" refers to pests that belong to the Order Lepidoptera including butterflies, moths and their larval stages. Exemplary lepidopterans include diamondback moth (*Plutella xylostella*) and cabbage looper (*Trichoplusia ni*).

In another preferred embodiment, the pest is *thrips*. As used herein, "*thrips*" refers to pests that belong to the Family Thripidae. Exemplary *thrips* include western flower *thrips* (*Frankliniella occidentalis*).

In another preferred embodiment, the pest is a whitefly. As used herein, "whitefly" refers to pests that belong to the Family Aleyrodidae. Exemplary whiteflies include tobacco whitefly (*Bemisia tabaci*).

In another preferred embodiment, the pest is a planthopper. As used herein, "planthopper", refers to pests that belong to the Infraorder Fulgoromorpha of the Order Hemiptera. Exemplary planthoppers include brown rice planthopper (*Nilaparvata lugens*).

In another preferred embodiment, the pest belongs to the infraclass Neoptera of the Class Insecta, the Subfamily Aphidinae of the Family Aphididae or the Parvorder *Heteroneura* of the Family Lepidoptera.

The following examples are presented by way of illustration and are not intended to limit the invention in any way.

EXAMPLES

Example 1. Phenotypic Characteristics of *T. album* HL-105-64-AC11

*Tolypocladium album* strain HL-105-64-AC11 was grown at 26° C. on a potato dextrose agar plate or in potato dextrose broth for 2-3 days. On plates, it forms larger, white, fluffy colonies. In liquid media, it produces both mycelia and spores. The liquid grown biomass can be used as an inoculum for fermentation studies. Its mycelia and spores in the liquid media can be observed under a microscope. A picture showing its typical colony morphology and microscopic observation of mycelia and spores is shown in FIG. 2.

Example 2. Terpendole and Nalanthalide Production of Various *Tolypocladium album* Strains Various *T. album* strains including HL-105-64-AC11 were grown in various media to determine terpendole and nalanthalide production. Specifically, a 500-milliliter shake flask containing 100 milliliters of fermentation medium was inoculated. The inoculated flask was incubated at 26° C. on a shaker at 250 revolutions per minute for 7-8 days. The fermentation broth was then analyzed for terpendoles and nalanthalide by high performance liquid chromatography.

The basic fermentation medium contained 2% w/v mannitol, 0.3% w/v yeast extract, 1.5% w/v soy flour, 0.1% w/v magnesium sulfate and 0.1% w/v monopotassium phosphate in water. Media 1-4 and 35 in Table 1, below, were modified from the basic fermentation medium composition for better yield of terpendoles. Results of this assay can be seen in Table 1, below.

TABLE 1

|  | Fermentation Medium | Terpendole C (mg/L) | Total Terpendole (mg/L) | Nalanthalide (mg/L) |
|---|---|---|---|---|
| *Tolypocladium pustulatum* (HL-90-POR-P01) | Medium 1 | 15.9 | 97.6 | 454 |
|  | Medium 2 | 0 | 4.21 | 0 |
|  | Medium 3 | 3.69 | 68.9 | 121 |
|  | Medium 4 | 0 | 37.1 | 179 |
| *T. album* (HL-89-CL01-Q10) | Medium 1 | 14 | 148.9 | 20.7 |
|  | Medium 2 | 8.14 | 155.8 | 31.9 |
|  | Medium 3 | 28.9 | 202.6 | 43.8 |
|  | Medium 4 | 5.64 | 69.7 | 0 |
| *T. album* (HL-103-22-R03) | Medium 1 | 33.5 | 198.7 | 26 |
|  | Medium 2 | 11.3 | 161.8 | 27.1 |
|  | Medium 3 | 20.2 | 229.4 | 41.7 |
|  | Medium 4 | 16.4 | 156.6 | 89.4 |
| *T. album* (HL-105-03-AD02) | Medium 1 | 106 | 268 | 97.3 |
|  | Medium 2 | 23.3 | 302.1 | 79.7 |
|  | Medium 3 | 150 | 323 | 122 |
|  | Medium 4 | 44.9 | 256.4 | 188 |
| *T. album* (HL-105-64-AC11) | Medium 1 | 75.6 | 426 | 0 |
|  | Medium 2 | 84.2 | 326 | 0 |
|  | Medium 3 | 24.9 | 200 | 0 |
|  | Medium 4 | 34.7 | 164.9 | 0 |
| *T. album* (*Chaunopycnis alba* ATCC 201787) | Medium 35 | 0.00 | 0.00 | 0.00 |

As seen in Table 1, above, *T. album* strain HL-105-64-AC11 produced the most terpendole C and total terpendoles. Further, HL-105-64-AC11 is the only *Tolypocladium* spp. strain assayed that did not produce the toxic compound nalanthalide in any of the media tested.

Example 3. Insecticidal Activity of *Tolypocladium album* Strain HL-105-64-AC11

An HL-105-64-AC11 fermentation broth was produced as in Example 2. The HL-105-64-AC11 fermentation broth was then diluted with water to 50%, 25% and 12.5% v/v and tested for control of diamondback moth (*Plutella xylostella*) and cabbage looper (*Trichoplusia ni*). Results of this assay can be seen in Table 2, below.

TABLE 2

|  | Dilution | | | | | |
|---|---|---|---|---|---|---|
|  | 12.5% | | 25% | | 50% | |
| % Efficacy | 24 hours | 48 hours | 24 hours | 48 hours | 24 hours | 48 hours |
| Diamondback moth | 30 | 50 | 57 | 70 | 70 | 92 |
| Cabbage looper | 22 | 64 | 62 | 94 | 90 | 100 |

As can be seen in Table 2, HL-105-64-AC11 fermentation broth was effective at controlling both diamondback moth and cabbage looper at all three dilutions.

Example 4. Miticidal Activity of *Tolypocladium album* Strain HL-105-64-AC11

An HL-105-64-AC11 fermentation broth was produced in shake flasks. The HL-105-64-AC11 fermentation broth was then diluted with water to 1.39% and 13.9% v/v and tested for control of twospotted spider mites (*Tetranychus urticae*) and green peach aphids (*Myzus persicae*). The results of these assays are summarized in Tables 3 and 4.

TABLE 3

|  | Dilution | | | |
|---|---|---|---|---|
|  | 1.39% | | 13.9% | |
| % Efficacy | 24 hours | 48 hours | 24 hours | 48 hours |
| Twospotted spider mite | 49.4 | 51.5 | 86.1 | 88.4 |

As can be seen in Table 3, HL-105-64-AC11 fermentation broth was effective at controlling twospotted spider mites at both dilutions.

TABLE 4

|  | Dilution | | | | | | | |
|---|---|---|---|---|---|---|---|---|
|  | 1.04% | | 3.125% | | 6.25% | | 12.5% | |
| % Efficacy | 24 hours | 48 hours | 24 hours | 48 hours | 24 hours | 48 hours | 24 hours | 48 hours |
| Green peach aphid | 48 | 67 | 92 | 98 | 90 | 100 | 97 | 100 |

As can be seen in Table 4, HL-105-64-AC11 fermentation broth was effective at controlling green peach aphids at four dilutions.

What is claimed is:

1. A pesticidal composition comprising a mixture of an effective amount of a biologically pure fungal strain of *Tolypocladium album*, having all the identifying characteristics of *Tolypocladium album* HL-105-64-AC11 having ATCC accession number PTA-124560 and a suitable carrier.

2. A method of controlling a pest comprising applying an effective amount of the pesticidal composition of claim 1 to a pest or the pest's environment.

3. The method of claim 2, wherein the pest is an insect.

4. The method of claim 2, wherein the pest is an aphid.

5. The method of claim 2, wherein the pest is a lepidopteran.

6. The method of claim 2, wherein the pest is a *thrips*.

7. The method of claim 2, where the pest is a mite.

8. The method of claim 2, wherein the pest is a whitefly.

9. The method of claim 4, wherein the aphid is selected from the group consisting of cotton aphid (*Aphis gossypii*), foxglove aphid (*Aulacorthum solani*), cabbage aphid (*Brevicoryne brassicae*), birdcherry-oat aphid (*Rhopalosiphum padi*) and green peach aphid (*Myzus persicae*).

10. The method of claim 5, wherein the lepidopteran is selected from the group consisting of diamondback moth (*Plutella xylostella*) and cabbage looper (*Trichoplusia ni*).

11. The method of claim 6, wherein the *thrips* is western flower *thrips* (*Frankliniella occidentalis*).

12. The method of claim 7, wherein the mite is a twospotted spider mite (*Tetranychus urticae*).

13. The method of claim 8, wherein the whitefly is a silverleaf whitefly (*Bemesia tabaci*).

14. The composition of claim 1, wherein the composition comprises produces terpendoles A, C, I, J, K, N, O and P.

15. The composition of claim 1, wherein the composition does not contain nalanthalide.

* * * * *

SEQUENCE LISTING

<160> NUMBER OF SEQ ID NOS: 1

<210> SEQ ID NO 1
<211> LENGTH: 572
<212> TYPE: DNA
<213> ORGANISM: Tolypocladium album

<400> SEQUENCE: 1

```
tttagaggaa gtaaaagtcg taacaaggtc tccgttggtg aaccagcgga gggatcatta      60
ccgagttatc aactcccaaa cccctgtgaa catacctgaa cgttgcctcg gcgggaccgc     120
cccggcgccc aactcgcggc ccggaccag gcgcccgccg gaggacccaa actcttgctt     180
taaacagtgg catactctct gagtctcaca aacaaaaaat gaatcaaaac tttcaacaac     240
ggatctcttg gctctggcat cgatgaagaa cgcagcgaaa tgcgataagt aatgtgaatt     300
gcagaattca gtgaatcatc gaatctttga acgcacattg cgcccgccag cattctggcg     360
ggcatgcctg tccgagcgtc atttcaaccc tcagggcccc cttcgcggg ggggacctgg     420 tgttgggggc cggccgccct gcgcgcgccg cccccgaaat gcagtggcga cctcgccgca     480
gcctcccctg cgtagtagca caacctcgca ccggagcgcg gagacggtca cgccgtaaaa     540
cgcccaactt tcaagagttg acctcggatc ag                                  572
```